United States Patent
Okamoto

(10) Patent No.: US 8,293,953 B2
(45) Date of Patent: Oct. 23, 2012

(54) METHOD FOR PRODUCING 1, 1-DICHLORO-2,2,3,3,3-PENTAFLUOROPROPANE

(75) Inventor: Hidekazu Okamoto, Chiyoda-ku (JP)

(73) Assignee: Asahi Glass Company, Limited, Tokyo (JP)

( * ) Notice: Subject to any disclaimer, the term of this patent is extended or adjusted under 35 U.S.C. 154(b) by 0 days.

(21) Appl. No.: 13/052,629

(22) Filed: Mar. 21, 2011

(65) Prior Publication Data

US 2011/0172469 A1 Jul. 14, 2011

Related U.S. Application Data

(63) Continuation of application No. 12/689,617, filed on Jan. 19, 2010.

(30) Foreign Application Priority Data

Jan. 19, 2009 (JP) .................................. 2009-009208

(51) Int. Cl.
*C07C 21/18* (2006.01)

(52) U.S. Cl. ........ 570/151; 570/135; 570/136; 570/156; 570/157

(58) Field of Classification Search .......................... None
See application file for complete search history.

(56) References Cited

U.S. PATENT DOCUMENTS

| 5,157,171 A | * | 10/1992 | Sievert et al. | ................... | 570/151 |
| 6,548,719 B1 | * | 4/2003 | Nair et al. | ...................... | 570/157 |

FOREIGN PATENT DOCUMENTS

| JP | 5-58924 | | 3/1993 |
| JP | 8-169850 | | 7/1996 |
| JP | 08169850 A | * | 7/1996 |
| JP | 3778298 | | 3/2006 |
| WO | WO 2008/060614 A2 | | 5/2008 |
| WO | WO 2010/074254 A1 | | 7/2010 |

OTHER PUBLICATIONS

Paul Tarrant, "Fluorine Chemistry Reviews", Marcel Dekker, Inc., vol. 8, 1967, pp. 39-71.

T. Tanuma, et al., "Metal Halide Catalysts to Synthesize dichloropentafluoropropanes by the reaction of dichlorofluoromethane with tetrafluoroethylene", Applied Catalysis A: General, 2008, 348 (2), pp. 236-240.

* cited by examiner

*Primary Examiner* — Sudhakar Katakam
(74) *Attorney, Agent, or Firm* — Oblon, Spivak, McClelland, Maier & Neustadt, L.L.P.

(57) ABSTRACT

To provide a method for producing 1,1-dichloro-2,2,3,3,3-pentafluoropropane (HCFC-225ca) at a high content ratio, which is useful as e.g. a starting material to obtain 1,1-dichloro-2,3,3,3-tetrafluoropropene (R1214ya).

The method comprises subjecting a starting material comprising one isomer or a mixture of at least two isomers of dichloropentafluoropropane (HCFC-225) and having a HCFC-225ca content of less than 60 mol %, to an isomerization reaction in the presence of a Lewis acid catalyst or a metal oxide catalyst so as to increase the HCFC-225ca content in the product to be higher than the content in the starting material.

22 Claims, 1 Drawing Sheet

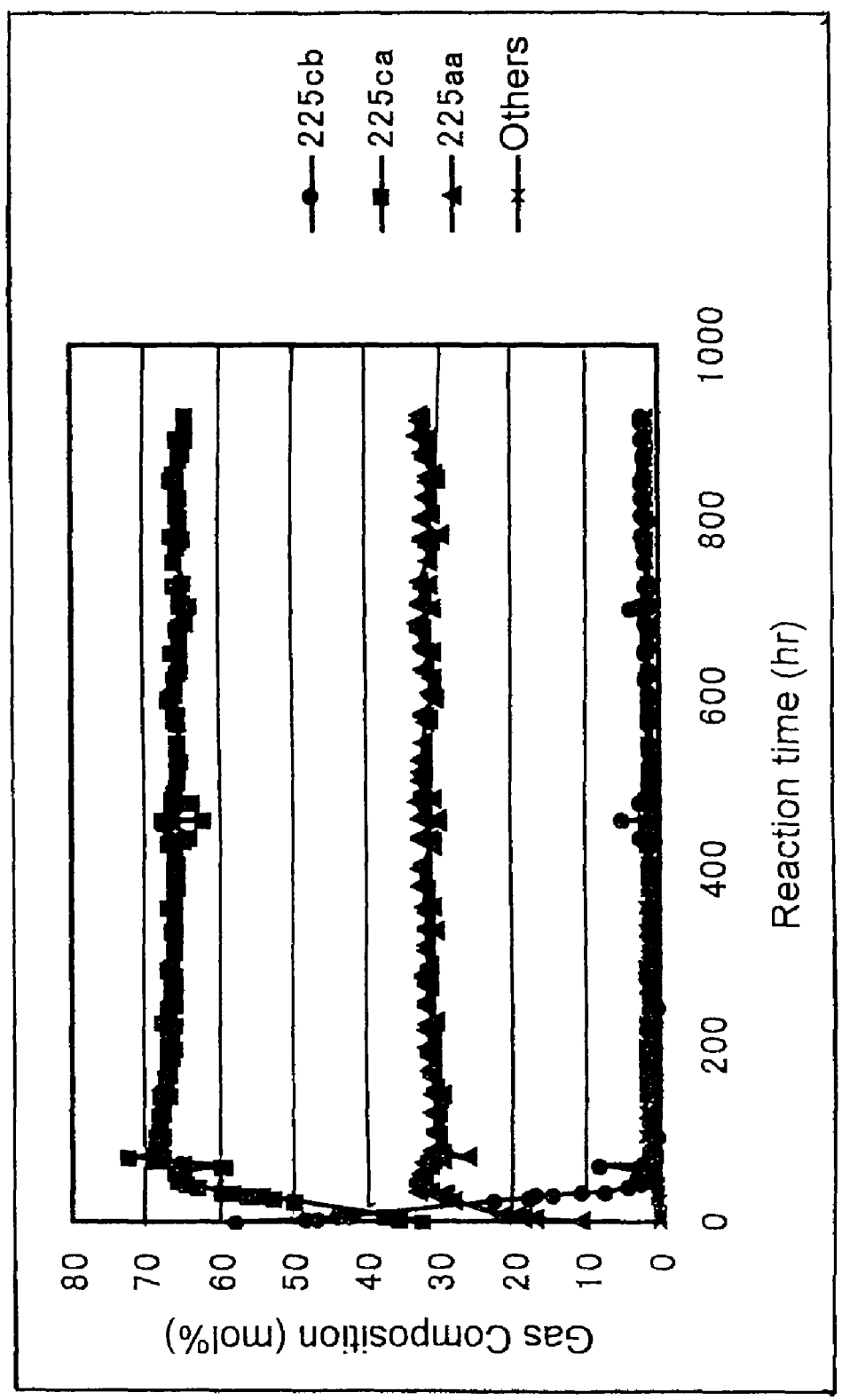

METHOD FOR PRODUCING 1,1-DICHLORO-2,2,3,3,3-PENTAFLUOROPROPANE

TECHNICAL FIELD

The present invention relates to a method for producing 1,1-dichloro-2,2,3,3,3-pentafluoropropane (HCFC-225).

BACKGROUND ART

Heretofore, various methods have been proposed as methods for producing dichloropentafluoropropane (HCFC-225) represented by a chemical formula $C_3HCl_2F_5$. For example, a method has been proposed which comprises contacting dichlorofluoromethane with tetrafluoroethylene in the presence of a modified aluminum chloride catalyst to obtain dichloropentafluoropropane, and a technique to apply isomerization to a mixture of various isomers of dichloropentafluoropropane obtained by this method, is disclosed (Patent Document 1).

However, by the isomerization method disclosed in Patent Document 1, it was not possible to obtain 1,1-dichloro-2,2,3,3,3-pentafluoropropane (HCFC-225ca) at a high content ratio.

On the other hand, in recent years, it has been studied to use 2,3,3,3-tetrafluoropropene (R1234yf) having a small ozone depletion potential, as a cooling medium of next generation to be substituted for 1,1,1,2-tetrafluoroethane (HFC-134a) being a greenhouse gas. It is considered to use 1,1-dichloro-2,3,3,3-tetrafluoropropene (R1214ya) as a starting material for preparing this R1234yf, and accordingly, usefulness of HCFC-225ca is expected as a starting material to obtain R1214ya. However, a method has not yet been found whereby HCFC-225ca can be efficiently obtained by increasing the content ratio of HCFC-225ca in the mixture of various isomers of HCFC-225.

Patent Document 1: U.S. Pat. No. 5,157,171.

SUMMARY OF THE INVENTION

Object to be Accomplished by the Invention

It is an object of the present invention to provide a method for producing 1,1-dichloro-2,2,3,3,3-pentafluoropropane (HCFC-225ca) useful as e.g. a starting material to obtain 1,1-dichloro-2,3,3,3-tetrafluoropropene (R1214ya) as a material to prepare 2,3,3,3-tetrafluoropropene (R1234yf) being an excellent cooling medium.

Means to Accomplish the Object

The present invention is to accomplish the above object and provides the following.

1. A method for producing 1,1-dichloro-2,2,3,3,3-pentafluoropropane, which comprises subjecting a starting material comprising one isomer or a mixture of at least two isomers of dichloropentafluoropropane and having a 1,1-dichloro-2,2,3,3,3-pentafluoropropane content of less than 60 mol %, to an isomerization reaction in the presence of a Lewis acid catalyst or a metal oxide catalyst so as to increase the 1,1-dichloro-2,2,3,3,3-pentafluoropropane content in the product to be higher than the content in the starting material.

2. The method for producing 1,1-dichloro-2,2,3,3,3-pentafluoropropane according to the above 1, wherein the starting material contains 1,3-dichloro-1,2,2,3,3-pentafluoropropane, and the 1,3-dichloro-1,2,2,3,3-pentafluoropropane is subjected to an isomerization reaction to form 1,1-dichloro-2,2,3,3,3-pentafluoropropane.

3. The method for producing 1,1-dichloro-2,2,3,3,3-pentafluoropropane according to the above 2, wherein the starting material further contains 2,2-dichloro-1,1,1,3,3-pentafluoropropane.

4. The method for producing 1,1-dichloro-2,2,3,3,3-pentafluoropropane according to any one of the above 1 to 3, wherein the isomerization reaction is carried out in a liquid phase in the presence of a Lewis acid catalyst at a temperature of from 0 to 150° C.

5. The method for producing 1,1-dichloro-2,2,3,3,3-pentafluoropropane according to any one of the above 1 to 3, wherein the isomerization reaction is carried out in a gas phase in the presence of a metal oxide catalyst at a temperature of from 50 to 500° C.

6. A method for producing 1,1-dichloro-2,3,3,3-tetrafluoropropene, which comprises bringing the 1,1-dichloro-2,2,3,3,3-pentafluoropropane obtained by the method as defined in any one of the above 1 to 5 into contact with an aqueous alkali solution in the presence of a phase transfer catalyst.

7. A method for producing 2,3,3,3-tetrafluoropropene, which comprises reacting the 1,1-dichloro-2,3,3,3-tetrafluoropropene obtained by the method as defined in the above 6 with hydrogen in the presence of a catalyst.

8. The method for producing 2,3,3,3-tetrafluoropropene according to the above 7, which is carried out in the presence of an inert gas.

Effects of the Invention

According to the present invention, it is possible to obtain, at a high content ratio (molar ratio), 1,1-dichloro-2,2,3,3,3-pentafluoropropane (HCFC-225ca) useful as a starting material to prepare 2,3,3,3-tetrafluoropropene (R1234yf) being an excellent cooling medium.

BRIEF DESCRIPTION OF THE DRAWING

FIG. 1 shows the change with time of the gas composition at the outlet of the reactor in Example 5 of the present invention.

PREFERRED EMBODIMENTS OF THE INVENTION

The method according to an embodiment of the present invention is characterized in that one isomer or a mixture of at least two isomers of dichloropentafluoropropane (HCFC-225), which has a 1,1-dichloro-2,2,3,3,3-pentafluoropropane (HCFC-225ca) content of less than 60 mol %, particularly less than 50 mol %, is used as a starting material, and this starting material is subjected to an isomerization reaction in the presence of a catalyst so as to increase the HCFC-225ca content in the reaction product to be higher than the content in the starting material. The HCFC-225ca content in the above mixture may be 0 mol %. The isomerization reaction can be carried out in a liquid phase using a Lewis acid as a catalyst. Otherwise, the isomerization reaction can be carried out in a gas phase using a metal oxide as a catalyst.

In the embodiment of the present invention, as the starting material for the isomerization reaction, it is possible to use any material so long as it is HCFC-225 (one isomer or a mixture of at least two isomers) which has a HCFC-225ca content of less than 60 mol %. For example, it is possible to use a mixture of isomers of HCFC-225 containing 1,3-dichloro-1,2,2,3,3-pentafluoropropane (HCFC-225cb) as the main component.

In the present invention, in order to obtain 1,1-dichloro-2,3,3,3-tetrafluoropropene (R1214ya) as a material for preparing 2,3,3,3-tetrafluoropropene (R1234yf) being a cooling medium, a mixture of isomers of HCFC-225 which contains HCFC-225ca, is contacted with an aqueous alkali solution in the presence of a phase transfer catalyst to carry out a reaction for selective dehydrofluorination of HCFC-225ca. The mixture of isomers as the starting material for this reaction contains HCFC-225cb, 2,2-dichloro-1,1,3,3,3-pentafluoropropane (HCFC-225aa), etc. in addition to HCFC-225ca. And such HCFC-225cb, HCFC-225aa, etc. will remain as they are without being reacted (dehydrofluorination). A mixture of isomers such as remaining HCFC-225cb, HCFC-225aa, etc. will be easily separated from the formed R1214ya by distillation. Such a separated mixture of isomers such as HCFC-225cb, HCFC-225aa, etc., can be used as a starting material for the isomerization reaction of the present invention. As the mixture of the isomers as the starting material for this reaction, a HCFC-225 product which is industrially produced, can be used. When dehydrofluorination reaction is carried out by using such a HCFC-225 product, HCFC-225ca in the HCFC-225 product selectively undergoes a dehydrofluorination reaction to form R1214ya. A mixture of HCFC-225 isomers remained as unreacted, can be used as a starting material containing HCFC-225cb as the main component.

Further, when such a starting material containing HCFC-225cb as the main component is isomerized, a mixture containing HCFC-225ca and HCFC-225aa as the main components will be formed. When a dehydrofluorination reaction is carried out by using this mixture, HCFC-225ca selectively undergoes the dehydrofluorination reaction to form R1214ya. A mixture of HCFC-225 isomers remained as unreacted can be used as a starting material containing HCFC-225aa as the main component.

In the embodiment of the present invention, the catalyst to be used for the isomerization reaction in a liquid phase is not particularly limited so long as it is a Lewis acid, but a halide containing at least one element selected from the group consisting of Al, Sb, Nb, Ta, W, Re, B, Sn, Ga, In, Zr, Hf and Ti, is preferably used. For example, it is possible to use a chloride such as $GaCl_2$, $GaCl_3$, $ZrCl_4$, $BCl_3$, $AlCl_3$, $HfCl_4$, $InCl_3$ or $TiCl_4$, or one having such a compound partially fluorinated, or a bromide or iodide such as $GaBr_3$, $GaI_3$, $HfBr_4$, $InI_3$ or $TiBr_4$, or one having such a compound partially chlorinated or fluorinated, such as $TiCl_2F_2$, $TiCl_2F_3$ or $ZrCl_2F_2$.

The amount of such a Lewis acid catalyst is preferably within a range of from 1 to 100 mol %, more preferably from 5 to 50 mol %, to the total amount of isomers of dichloropentafluoropropane (one isomer or a mixture of at least two isomers) as the starting material.

In a case where the isomerization reaction is carried out in a liquid phase, a solvent for the reaction may be added. The reaction temperature is preferably within a range of from 0 to 150° C., more preferably from 30 to 100° C. The reaction time is usually from 0.5 to 200 hours, preferably from 1 to 100 hours, although it depends also on the reaction temperature or the type of the Lewis acid catalyst.

The catalyst to be used for the isomerization reaction in a gas phase is not particularly limited so long as it is a metal oxide, but an oxide of at least one element selected from the group consisting of Al, Sb, Nb, Ta, W, Re, B, Sn, Ga, In, Zr, Hf and Ti, is preferred, and alumina or zirconia is more preferred.

In the isomerization reaction in a gas phase, the reaction temperature is preferably from 50 to 500° C., more preferably from 100 to 450° C., further preferably from 200 to 400° C. The reaction pressure is preferably within a range of from 0 to 0.2 kg/cm², particularly preferably within a range of from 0 to 1 kg/cm². The reaction time is usually from 10 to 180 seconds, particularly preferably from 20 to 90 seconds, although it depends also on the reaction temperature or the type of the metal oxide catalyst. In the isomerization reaction, the mixture of isomers of HCFC-225 as the starting material may be diluted with an inert gas such as nitrogen and then supplied for the reaction. The molar ratio of the mixture of isomers of HCFC-225 to the inert gas (the mixture of isomers of HCFC-225:the inert gas) is preferably from 1:0.1 to 1:10, more preferably from 1:0.1 to 1:5.

In the embodiment of the present invention, the starting material comprising isomers of HCFC-225 (one isomer or a mixture of at least two isomers) is subjected to an isomerization reaction in the presence of the above-mentioned Lewis acid catalyst or metal oxide catalyst under the above-mentioned reaction conditions, whereby it is possible to form HCFC-225ca and it is possible to substantially increase the HCFC-225ca content in the reaction product over the content in the starting material. By the isomerization reaction of the present invention, the HCFC-225ca content is increased to be higher by at least 10 mol %, more preferably by 30 mol %, than the content in the starting material.

Particularly, in a case where the starting material contains HCFC-225cb, this HCFC-225cb undergoes an isomerization reaction to form a mixture of isomers containing HCFC-225ca as the main component, whereby the HCFC-225cb content (molar ratio) in the starting material decreases, and instead, the HCFC-225ca content increases as compared with the content in the starting material.

Further, in a case where the starting material contains HCFC-225aa, and the content of HCFC-225aa present in the starting material is larger than the equilibrium composition at the isomerization reaction temperature, the HCFC-225aa content in the starting material decreases, and instead, the HCFC-225ca content increases.

Further, in order to let HCFC-225ca form by the isomerization reaction to increase the HCFC-225ca content (molar ratio) in the reaction product over the content in the starting material, the HCFC-225 ca content in the starting material must be less than 60 mol % for the following reason.

That is, in a case where a mixture of various isomers of HCFC-225 is subjected to an isomerization reaction, for example, at 25° C., the HCFC-225ca content in an equilibrium state will be from 78 to 80 mol %. If the reaction temperature becomes high, the value of this content will decrease, but it will not be less than 60 mol %. Accordingly, if the HCFC-225ca content in the starting material is 60% or higher (for example 70 mol %), it is likely that by the isomerization reaction, the HCFC-225ca content becomes lower than the content in the starting material, but when the HCFC-225ca content is less than 60 mol %, the HCFC-225ca content in the product of the isomerization reaction will increase as compared with the content in the starting material. That is, it is possible to let HCFC-225ca form by the isomerization reaction of the starting material thereby to increase the content to be higher than in the starting material.

Thus, according to the embodiment of the present invention, it is possible to obtain HCFC-225ca at a high content ratio among various isomers of HCFC-225. And, HCFC-225ca thus obtained can be used as a starting material to form R1214ya.

To form R1214ya by using HCFC-225ca as a starting material, it is possible to employ, for example, a method which comprises contacting the starting material with an aqueous alkali solution in the presence of a phase transfer catalyst so that only the HCFC-225ca be selectively dehydrofluorinated.

Here, the aqueous alkali solution is not particularly limited so long as it is an aqueous solution of a basic compound capable of carrying out the dehydrofluorination reaction. However, it is preferred to employ an aqueous solution of sodium hydroxide, potassium hydroxide or the like. The alkali concentration in the aqueous alkali solution is not particularly limited, but it is preferably from 0.5 to 40 mass %. Further, the amount of the aqueous alkali solution is not particularly limited, but it is preferably adjusted so that the amount of an alkali will be from 0.5 to 1.5 mol equivalent, more preferably from 0.8 to 1.2 mol equivalent, to the amount of HCFC-225ca to be used for the reaction. On the other hand, as the phase transfer catalyst, a phase transfer catalyst which is commonly employed, can be used without any particular restriction. Specifically, it is possible to use, for example, a quaternary ammonium salt or quaternary phosphonium salt substituted by a hydrocarbon group, or a crown ether. The amount of the phase transfer catalyst is preferably from 0.001 to 5 mass %, more preferably from 0.01 to 1 mass %, to the mass of HCFC-225ca as the starting material. Further, the reaction temperature in the above dehydrofluorination reaction is not particularly limited, but it is preferably from 0 to 80° C., more preferably from 0 to 50° C.

R1214ya thus obtained, is further reacted with hydrogen in the presence of a catalyst (e.g. a Pd catalyst) to obtain 2,3,3,3-tetrafluoropropene (R1234yf) as a cooling medium to be substituted for a greenhouse gas.

The above catalyst may, for example, be a catalyst having palladium supported on a carrier, or a catalyst containing palladium as the main component and having, supported on a carrier, a mixture prepared by adding palladium and at least one member selected from Group 10 elements other than palladium, Group 8 elements, Group 9 elements and gold. The Group 10 elements other than palladium, Group 8 so elements and Group 9 elements include, iron, cobalt, nickel, ruthenium, rhodium, iridium, osmium and platinum. Further, the amount of metals other than palladium to be added to palladium, is preferably from 0.01 to 50 parts by mass per 100 parts by mass of palladium. Here, a composite catalyst having other metals added to palladium has an effect such that the catalyst durability tends to be higher than one made of palladium alone.

As the carrier to support the above palladium or a metal mixture containing palladium as the main component, activated carbon or a metal oxide such as alumina, zirconia or silica may, for example, be used. Among them, activated carbon is preferably employed from the viewpoint of the activity, durability or selectivity in the reaction. As the activated carbon, it is possible to use one prepared from a material such as wood, charcoal, fruit shell, coconut shell, peat, lignite or coal, and one obtained from a plant material is preferred to one obtained from a mineral material. Particularly preferred is a coconut shell activated carbon. With respect to the shape of the carrier, it is possible to employ a molded carbon having a length of from about 2 to 5 mm, granulated carbon of from about 4 to 50 mesh or pelletized carbon, but granulated carbon of from 4 to 20 mesh or molded carbon is preferred.

The reaction to form R1234yf is preferably carried out by a gas phase reduction method wherein heated gasified R1214ya and hydrogen are passed through a reactor packed with a catalyst at a temperature of from 130 to 250° C., preferably from 150 to 200° C. to contact them with the catalyst. The molar ratio of R1214ya to hydrogen supplied (R1214ya:$H_2$) is preferably from 1:0.5 to 1:10, more preferably from 1:0.5 to 1:5. The reaction pressure is usually atmospheric pressure or natural pressure, whereby R1234yf-forming reaction sufficiently proceeds. The contact time with the catalyst may be set within a range of usually from 4 to 60 seconds, preferably from 8 to 40 seconds. Further, to control an excessive increase of the temperature, the reaction may be carried out by diluting the atmosphere with an inert gas such as nitrogen. The molar ratio of hydrogen and the inert gas to be supplied ($H_2$: the inert gas) is preferably from 1:0.1 to 1:10, more preferably from 1:0.5 to 1:4.

EXAMPLES

Now, the present invention will be described in detail with reference to Examples, but it should be understood that the present invention is by no means restricted to such Examples.

Example 1

Firstly, a Lewis acid catalyst was prepared as follows. That is, a Dimroth condenser having a cooling medium cooled to −20° C., circulated, was set on a three-necked flask (internal capacity: 500 mL), 50 g (0.375 mol) of aluminum trichloride ($AlCl_3$) was charged thereto and cooled to 0° C., and then, 175 mL (262.5 g; 1.9 mol) of trichlorofluoromethane ($CFCl_3$) was slowly dropwise added with stirring.

Isomerization of trichlorofluoromethane proceeded, while accompanied by generation of a low boiling point gas. And, along with the progress of isomerization, a halogen exchange reaction proceeded between chlorofluoromethane as a substrate and aluminum trichloride ($AlCl_3$) as a catalyst, to form a fluorinated aluminum halide. The reaction was continued for one hour, whereupon a volatile component was removed, and the catalyst was dried. Thus, a partially fluorinated aluminum chloride was obtained.

Then, to a glass reactor (internal capacity: 1 L) provided with a Dimroth condenser cooled to 0° C., 10 g of the partially fluorinated aluminum chloride obtained by the above reaction was introduced as a catalyst, and 609 g (3.0 mol) of a starting material liquid being a mixture of isomers of chloropentafluoropropane (HCFC-225) was added thereto. The composition of the starting material liquid (the molar ratio of isomers) is shown in Table 1.

Here, this starting material liquid was a residue (the residual product) obtained by reacting ASAHIKLIN AK225 (tradename of Asahi Glass Company, Limited; comprising HCFC-225ca, HCFC-225cb and other isomers) being a mixture of isomers of HCFC-225 in an aqueous alkali solution in the presence of a phase transfer catalyst (tetrabutylammonium bromide) to selectively dihydrogen fluorinating HCFC-225ca, subjecting the obtained crude liquid to liquid separation, then distilling the organic phase and recovering R1214ya (boiling point: 45° C.).

Then, after adding such a starting material liquid, the temperature in the reactor was raised to 50° C., and a reaction was carried out for 20 hours with stirring. After the reaction, the liquid was subjected to filtration to remove the catalyst and to recover 600 g of the reaction product liquid. Then, the obtained reaction product liquid was analyzed by gas chromatography to obtain the composition of the reaction products. The results are shown in Table 1. Here, in the Table, HCFC-225aa represents 2,2-dichloro-1,1,3,3,3-pentafluoropropane.

TABLE 1

| | Molar ratio (%) | |
|---|---|---|
| | Composition of starting material liquid | Composition of reaction product liquid |
| HCFC-225ca | 0 | 75 |
| HCFC-225cb | 99.5 | 1 |
| HCFC-225aa | 0 | 19 |
| Other isomers | 0.5 | 5 |

From the results in Table 1, it is evident that the isomerization reaction of HCFC-225cb in the starting material proceeded to form HCFC-225ca which was not present in the starting material, whereby the content of this HCFC-225ca increased to at least 70 mol %.

Examples 2 to 4

Firstly, a catalyst was prepared as follows. That is, a catalyst of spherical activated alumina having a particle size of 2 mm (specific surface area: 280 m$^2$/g, "ACBM-1", manufactured by Catalysts & Chemicals Industries Co., Ltd.) was packed in a reaction tube made of Inconel (registered trademark) 600 and having an inner diameter of 2.54 cm and a length of 100 cm and immersed in a salt bath. A gas mixture of nitrogen/Freon R-12 ($CCl_2F_2$) of 2/1 (mol/mol) heated to 250° C. was passed for a contact time of 20 seconds for 4 hours to activate the catalyst.

Then, the temperature of the salt bath was raised to the temperature identified in Table 2, and a mixture of isomers of HCFC-225 prepared in the same manner as in Example 1 was passed under the conditions shown in Table 2 to carry out the isomerization reaction. The gas composition at the outlet of the reactor was analyzed by gas chromatography to carry out the analysis of the composition of the reaction products. The results are shown in Table 2.

TABLE 2

| | | Composition of starting material | Ex. 2 | Ex. 3 | Ex. 4 |
|---|---|---|---|---|---|
| Reaction conditions | Reaction temperature | — | 250° C. | 300° C. | 350° C. |
| | Starting material supply ratio (molar ratio) (HCFC-225/N$_2$) | — | 1/2 | 1/2 | 1/2 |
| | Contact time | — | 20 seconds | 20 seconds | 20 seconds |
| Composition of crude gas | CClF$_2$CF$_2$CHClF (HCFC-225cb) | 99.5 mol % | 20 mol % | 1 mol % | 1 mol % |
| | CF$_3$CF$_2$CHCl$_2$ (HCFC-225ca) | 0 mol % | 58 mol % | 64 mol % | 60 mol % |
| | CF$_3$CCl$_2$CHF$_2$ (HCFC-225aa) | 0 mol % | 21 mol % | 34 mol % | 36 mol % |
| | Other isomers | 0.5 mol % | 1 mol % | 1 mol % | 3 mol % |

Example 5

The reaction was carried out in the same manner as in Example 3, and while the analysis of the gas composition at the outlet of the reactor was carried out with time, the reaction was continued for 940 hours. FIG. 1 shows the results obtained by analyzing the change with time of the gas composition at the outlet of the reactor.

From the results in FIG. 1, it was confirmed that no deterioration of the catalyst was observed even after expiration of 940 hours.

Example 6

Using the reaction crude liquid recovered in Example 1, 1,1-dichloro-2,3,3,3-tetrafluoropropene ($CF_3CF_3CCl_2$, R1214ya) was produced by the following method.

To a glass reactor having an internal capacity of 1 L and provided with a Dimroth condenser cooled to 0° C., 3 g of tetrabutylammonium bromide (TBAB) as a phase transfer catalyst, 129 g of potassium hydroxide (2.30 mol), 220 g of water and 600 g (2.96 mol) of the above-mentioned recovered composition were charged and then gradually heated with stirring to carry out a reaction at 45° C. for one hour. After completion of the reaction, a part of the organic phase of the reaction crude liquid was recovered, and the composition was analyzed by gas chromatography (GC). The analytical results are shown in Table 3.

Further, after the GC analysis, the reaction crude liquid separated into two phases of an organic phase and an aqueous phase was subjected to liquid separation, and the organic phase was charged and distilled in a distillation column having a capacity of 1 L and an ability of theoretical plate number of 10 plates. As a result of the distillation, it was possible to recover 384 g (2.10 mol) of R1214ya having a purity of 99.5% (boiling point: 45° C.).

TABLE 3

| | Mol composition (%) | |
|---|---|---|
| | Composition of starting material liquid | Composition of reaction crude liquid |
| HCFC-225ca | 75 | 0 |
| HCFC-225cb | 1 | 1 |
| HCFC-225aa | 19 | 19 |
| Other isomers of HCFC-225 | 5 | 5 |
| R1214ya | 0 | 75 |

A catalyst of activated carbon having 2 mass % of palladium supported (tradename: Shirasagi C2X, manufactured by Takeda Pharmaceutical Company Limited) was packed into a reaction tube made of Inconel (registered trademark) 600 having an inner diameter of 2.54 cm and a length of 100 cm, and immersed in a salt bath. Using 1,1-dichloro-2,3,3,3-tetrafluoropropene ($CF_3CF{=}CCl_2$, R1214ya) obtained by the above-described method, a reduction reaction was carried out under the reaction conditions identified in Table 4 to produce 2,3,3,3-tetrafluoropropene ($CF_3CF{=}CH_2$, R1234yf.)

Confirmation of the reaction products was carried out by analyzing the gas discharged from the reactor by gas chromatography and calculating the crude gas composition. The results are shown at the lower portion in Table 4.

TABLE 4

| | | |
|---|---|---|
| Reaction conditions | Reaction temperature | 200° C. |
| | Starting material supply ratio R1214ya/H$_2$/N$_2$ | 1/2/2 (molar ratio) |
| | Contact time | 53 seconds |
| Composition of crude gas | CF$_3$CF=CCl$_2$ (R1214ya) | 0% |
| | CF$_3$CF=CH$_2$ (R1234yf) | 72% |
| | Others | 28% |

Example 7

As the residue in the distillation to recover R1214ya in Example 6, a composition shown in Table 5 was recovered. Using this composition as a starting material, an isomerization reaction was carried out by the same method as the method shown in Example 3. The gas composition at the outlet of the reactor was analyzed by gas chromatography thereby to carry out the analysis of the composition of the reaction products. The results are shown in Table 5.

TABLE 5

| | Mol composition (%) | |
|---|---|---|
| | Composition of starting material liquid | Composition of reaction crude gas |
| HCFC-225ca | 0 | 62 |
| HCFC-225cb | 5 | 1 |
| HCFC-225aa | 76 | 35 |
| Other isomers of HCFC-225 | 19 | 2 |

INDUSTRIAL APPLICABILITY

From HCFC-225ca obtained by the present invention, it is possible to efficiently produce R1234yf useful as a new cooling medium, via R1214ya.

The entire disclosure of Japanese Patent Application No. 2009-009208 filed on Jan. 19, 2009 including specification, claims, drawings and summary is incorporated herein by reference in its entirety.

What is claimed is:

1. A method for producing 1,1-dichloro-2,3,3,3-tetrafluoropropene comprising contacting a mixture of dichloropentafluoropropane comprising 1,1-dichloro-2,2,3,3,3-pentafluoropropane with an aqueous alkali solution in the presence of a phase transfer catalyst, wherein said mixture of dichloropentafluoropropane is obtained by subjecting a starting material comprising one isomer or a mixture of at least two isomers of dichloropentafluoropropane and having a 1,1-dichloro-2,2,3,3,3-pentafluoropropane content of less than 60 mol %, to an isomerization reaction in the presence of a Lewis acid catalyst or a metal oxide catalyst so as to increase the 1,1-dichloro-2,2,3,3,3-pentafluoropropane content in the product to be higher than the content in the starting material.

2. The method of claim 1, wherein said starting material comprises 1,3-dichloro-1,2,2,3,3-pentafluoropropane, and said 1,3-dichloro-1,2,2,3,3-pentafluoropropane is subjected to an isomerization reaction to form 1,1-dichloro-2,2,3,3,3-pentafluoropropane.

3. The method of claim 2, wherein said starting material further comprises 2,2-dichloro-1,1,1,3,3-pentafluoropropane.

4. The method of claim 1, wherein said isomerization reaction is carried out in a liquid phase in the presence of a Lewis acid catalyst at a temperature of from 0 to 150° C.

5. The method of claim 1, wherein said isomerization reaction is carried out in a gas phase in the presence of a metal oxide catalyst at a temperature of from 50 to 500° C.

6. A method for producing 2,3,3,3-tetrafluoropropene, which comprises reacting the 1,1-dichloro-2,3,3,3-tetrafluoropropene obtained by the method as defined in claim 1 with hydrogen in the presence of a catalyst.

7. The method of claim 6, wherein said 1,1-dichloro-2,3,3,3-tetrafluoropropene is reacted with hydrogen in the presence of a catalyst and an inert gas.

8. The method of claim 1, wherein said aqueous alkali solution comprises at least one alkali selected from the group consisting of sodium hydroxide and potassium hydroxide.

9. The method of claim 1, wherein said aqueous alkali solution has an alkali concentration of from 0.5 to 40 mass %.

10. The method of claim 1, wherein an amount of said aqueous alkali solution is 0.5 to 1.5 mol equivalents to an amount of 1,1-dichloro-2,2,3,3,3-pentafluoropropane.

11. The method of claim 1, wherein said phase transfer catalyst is at least one catalyst selected from the group consisting of a quaternary ammonium salt, a quaternary phosphonium salt substituted by a hydrocarbon group and a crown ether.

12. The method of claim 1, wherein said phase transfer catalyst is in an amount of 0.0001 to 5 mass % to a mass of said 1,1-dichloro-2,2,3,3,3-pentafluoropropane.

13. The method of claim 1, wherein dehydrofluorination is conducted.

14. The method of claim 1, wherein dehydrofluorination is conducted at a temperature of from 0 to 80° C.

15. The method of claim 1, wherein dehydrofluorination is conducted at a temperature of from 0 to 50° C.

16. The method of claim 1, wherein said 1,1-dichloro-2,2,3,3,3-pentafluoropropane is selectively dehydrofluorinated.

17. The method of claim 1, wherein a content of said 1,1-dichloro-2,2,3,3,3-pentafluoropropane is increased by at least 10 mol % relative to said starting material.

18. The method of claim 1, wherein a content of said 1,1-dichloro-2,2,3,3,3-pentafluoropropane is increased by at least 30 mol % relative to said starting material.

19. The method of claim 3, wherein a content of said 2,2-dichloro-1,1,1,3,3-pentafluoropropane in said starting material is decreased during said isomerization reaction.

20. The method of claim 1, wherein a content of said 1,1-dichloro-2,2,3,3,3-pentafluoropropane in said product is from 78-80 mol %.

21. The method of claim 11, wherein said mixture of dichloropentafluoropropane comprises 1,1-dichloro-2,2,3,3,3-pentafluoropropane, 1,3-dichloro-1,2,2,3,3-pentafluoropropane and 2,2-dichloro-1,1,3,3,3-pentafluoropropane and said 1,3-dichloro-1,2,2,3,3-pentafluoropropane and 2,2-dichloro-1,1,3,3,3-pentafluoropropane are not reacted by contacting with said aqueous alkali solution.

22. The method of claim 1, wherein said mixture of dichloropentafluoropropane comprises 1,1-dichloro-2,2,3,3,3-pentafluoropropane and 2,2-dichloro-1,1,3,3,3-pentafluoropropane.

* * * * *